(12) United States Patent
Pajouhesh et al.

(10) Patent No.: US 6,784,202 B1
(45) Date of Patent: Aug. 31, 2004

(54) CUBANE DERIVATIVES AS METABOTROPIC GLUTAMATE RECEPTOR AGONISTS OR ANTAGONISTS AND PROCESS FOR THEIR PREPARATION

(75) Inventors: Hassan Pajouhesh, Vancouver (CA); Kenneth Curry, Vancouver (CA)

(73) Assignee: Prescient NeuroPharma Inc., Vancouver (CA)

( * ) Notice: Subject to any disclaimer, the term of this patent is extended or adjusted under 35 U.S.C. 154(b) by 0 days.

(21) Appl. No.: 09/673,473

(22) PCT Filed: Apr. 19, 1999

(86) PCT No.: PCT/CA99/00311

§ 371 (c)(1),
(2), (4) Date: Nov. 29, 2000

(87) PCT Pub. No.: WO99/54280

PCT Pub. Date: Oct. 28, 1999

(30) Foreign Application Priority Data

Apr. 17, 1998 (CA) .............................................. 2235119

(51) Int. Cl.[7] ..................... A61K 31/382; C07D 335/18

(52) U.S. Cl. ......................................... 514/437; 549/26

(58) Field of Search ............................. 549/26; 514/437

(56) References Cited

PUBLICATIONS

Kozikowski, A., et al. "α–Substituted Quisqualic Acid Analogs: New Metabotrpic Glutamate Receptor Group II Selective Antagonists." Bioorg.Med.Chem.Lett. 8 (1998) pp. 447–452.

Toms, N., et al., "The effects of (RS)–α–cyclopyl–4–phosphonophenylglycine ((RS)–CPPG), a potent and selective metabotropic glutamate receptor antagonist" British Journal of Pharmacologyvol. 119, No. 5, (Jan. 1, 1996) pp. 851–854, XP 000618728.

Marinozzi, M., et al., "Asymmetric Synthesis of Enantiomerically Pure (2S,1'S,2'S,3'R)–Phenylcarboxycyclopropylglycine (PCCG–4): A Potent and selective ligand at Group II Metabotropic Glutamate Receptors" Bioorg.Med.Chem. Lett. vol. 6, No 18 (1996) pp. 2243–2246.

Pellicciari, R., et al., "Synthesis and Preliminary Evaluation of (S)–2–(4'–Carboxycubyl)Glycine, a New Selective mGluR1 Antagonist." Bioorg.Med.Chem.Lett. 8 (1998), pp. 1569–1574.

Primary Examiner—Joseph K. McKane
Assistant Examiner—Rebecca Anderson
(74) Attorney, Agent, or Firm—Nath & Associates PLLC; Jerald L. Meyer; Gary M. Nath (57) ABSTRACT

The present invention relates to therapeutically active cubane compounds, a method of preparing the same, and to pharmaceutical compositions comprising the compounds. The novel compounds are useful in treating diseases of the central nervous system related to the metabotropic glutamate receptor system.

10 Claims, 1 Drawing Sheet

Figure 1

CUBANE DERIVATIVES AS METABOTROPIC GLUTAMATE RECEPTOR AGONISTS OR ANTAGONISTS AND PROCESS FOR THEIR PREPARATION

FIELD OF THE INVENTION

This invention pertains to therapeutically active cubane derivatives, a method for preparing the same, pharmaceutical compositions comprising the compounds and a method of treating diseases of the Central Nervous System (CNS) therewith.

BACKGROUND OF THE INVENTION

The acidic amino acid L-Glutamate is recognized as the major excitatory neurotransmitter in the CNS. The receptors that respond to L-Glutamate are called excitatory amino acid receptors. The excitatory amino acid receptors are thus of great physiological importance, playing a role in a variety of physiological processes, such as long-term potentiation (learning and memory), the development of synaptic plasticity, motor control, respiratory and cardiovascular regulation, and sensory perception.

Excitatory amino acid receptors are classified into two general types and both are activated by L-Glutamic acid and its analogs. Receptors activated by L-Glutamic acid that are directly coupled to the opening of cation channels in the cell membrane of the neurons are termed "ionotropic." This type of receptor has been subdivided into at least three subtypes, which are defined by the depolarizing actions of the selective agonists N-Methyl-D-aspartate (NMDA), α-Amino-3-hydroxy-5-methylisoxazole-4-propionic acid (AMPA), and Kainic acid (KA).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function (Schoepp and Conn, *Trends in Pharmacological Science*, 14:13, 1993). Both types of receptors appear not only to mediate normal synaptic transmission along excitatory pathways but also to participate in the modification of synaptic connections during development and throughout life.

So far eight different clones of the G-protein-coupled metabotropic glutamate receptors (mGluRs) have been identified (Knopfel et al., 1995, *J. Med Chem.*, 38, 1417–1426). These receptors function to modulate the presynaptic release of L-Glutamate, and the postsynaptic sensitivity of the neuronal cell to L-Glutamate excitation. Based on pharmacology, sequence homology and the signal transduction pathway that they activate, the mGluRs have been subclassified into three groups. The mGluR1 and mGluR5 receptors form group 1. They are coupled to hydrolysis of phosphatidylinositol (PI) and are selectively activated by (RS)-3,5-dihydroxyphenylglycine (Brabet et al., *Neuropharmacology*, 34, 895–903, 1995). Group II comprises mGluR$_2$ and mGluR$_3$ receptors. They are negatively coupled to adenylate cyclase and are selectively activated by (2S,1'R,2'R,3'R)-2-(2,3-dicarboxycyclopropyl)glycine (DCG-IV; Hayashi et al., *Nature*, 366, 687–690, 1993). Finally, the mGluR$_4$, mGluR$_6$, mGluR$_7$ and mGluR$_8$ receptors belong to group III. They are also negatively coupled to adenylate cyclase and are selectively activated by (L)-2-amino-4phosphonobutyric acid (L-AP4; Knopfel et al., 1995, *J. Med. Chem.*, 38, 1417–1426).

Agonists and antagonists of these receptors are believed useful for the treatment of acute and chronic neurodegenerative conditions, and as antipsychotic, anticonvulsant, analgesic, anxiolytic, antidepressant, and anti-emetic agents. Antagonists and agonists of neural receptors are classified as selective for a particular receptor or receptor subtype, or as non-selective. Antagonists may also be classified as competitive or non-competitive. While competitive and non-competitive antagonists act on the receptors in a different manner to produce similar results, selectivity is based upon the observations that some antagonists exhibit high levels of activity at a single receptor type, and little or no activity at other receptors. In the case of receptor-specific diseases and conditions, the selective agonists and antagonists are of the most value.

Compounds such as L-Glutamic acid, Quisqualic acid and Ibotenic acid are known to act as non-selective agonists on the mGluRs, while selective ionotropic glutamate receptor agonists such as NMDA, AMPA and Kainic acid have little effect on these receptors. Recently a few compounds without activity at the ionotropic glutamate receptors but with activity at the metabotropic receptors have been identified. These include trans-ACPD (trans (1S,3R-1-aminocyclopentane-1,3-dicarboxylic acid), the partial agonist L-AP3 (L-2-amino-3-phosphonopropionic acid; Palmer, E., Monaghan, D. T. and Cotman, C. W. *Eur. J. Pharmacol.* 166, 585–587, 1989; Desai, M. A. and Conn, P. J. *Neuroscience Lett.* 109, 157–162, 1990; Schoepp, D. D. et al., *J Neurochemistry.* 56, 1789–1796, 1991; Schoepp D. D. and Johnson B. G. *J. Neurochemistry* 53, 1865–1613, 1989), L-AP4 (L-2-amino-4-phosphonobutyric acid) which is an agonist at the mGluR$_4$ receptor (Thomsen C. et al., *Eur. J. Pharmacol.* 227, 361–362, 1992) and some of the isomers of CCG (2-(carboxycyclopropyl)glycines) especially L-CCG-I and L-CCG-II (Hayashi, Y. et al., *Br. J Pharmacol.* 107, 539–543, 1992).

Very few selective antagonists at the mGluRs have been reported. However some phenylglycine derivatives, S-4CPG (S-4carboxyphenylglycine), S-4C3HPG (S-4-carboxy-3-hydroxyphenylglycine) and S-MCPG (S-α-methyl-4-carboxyphenylglycine) have been reported to antagonize trans-ACPD-stimulated phosphoinositide hydrolysis and thus possibly act as antagonists at mGluR$_1$ and mGluR$_5$ subtypes (Thomsen, C. and Suzdak, P, *Eur. J. Pharmacol.* 245, 299, 1993).

Research directed towards mGluRs is beginning to show that mGluRs may be implicated in a number of normal as well as pathological mechanisms in the brain and spinal cord. For example, activation of these receptors on neurons can: influence levels of alertness, attention and cognition; protect nerve cells from excitotoxic damage resulting from ischemia, hypoglycemia and anoxia; modulate the level of neuronal excitation; influence central mechanisms involved in controlling movement; reduce sensitivity to pain; reduce levels of anxiety.

The use of compounds active at the mGluRs for the treatment of epilepsy is corroborated by investigations of the influence of trans-ACPD on the formation of convulsions (Sacaan and Schoepp, *Neuroscience Lett.* 139, 77, 1992) and that phosphoinositide hydrolysis mediated via mGluR is increased after kindling experiments in rats (Akiyama et al. *Brain Res.* 569, 71, 1992). Trans-ACPD has been shown to increase release of dopamine in the rat brain, which indicates that compounds acting on the mGluRs might be usable for the treatment of Parkinson's disease and Huntington's Chorea (Sacaan et al., *J. Neurochemistry* 59, 245, 1992).

Trans-ACPD has also been shown to be a neuroprotective agent in a medial cerebral artery occlusion (MCAO) model in mice(Chiamulera et al. *Eur. J. Pharmacol.* 215, 353, 1992), and it has been shown to inhibit NMDA-induced neurotoxicity in nerve cell cultures (Koh et al., *Proc. Natl. Acad. Sci. USA* 88, 9431, 1991). The mGluR-active compounds are also implicated in the treatment of pain. This is proved by the fact that antagonists at the metabotropic glutamate receptors antagonize sensory synaptic response to noxious stimuli of thalamic neurons (Eaton, S. A. et al., *Eur. J. Neuroscience*, 5, 186, 1993).

The use of compounds active at the mGluRs for treatment of neurological diseases such as senile dementia have also been indicated by the findings of Zheng and Gallagher (*Neuron* 9, 163, 1992) and Bashir et al. (*Nature* 363, 347, 1993) who demonstrated that activation of mGluRs is necessary for the induction of long-term potentiation (LTP) in nerve cells (septal nucleus, hippocampus) and the finding that long-term depression is induced after activation of metabotropic glutamate receptors in cerebellar granule cells (Linden et al. *Neuron* 7, 81, 1991).

Thus compounds that demonstrate either activating or inhibiting activity at mGluRs have therapeutic potential for the treatment of neurological disorders. These compounds have application as new drugs to treat both acute and chronic neurological disorders, such as stroke and head injuries; epilepsy; movement disorders associated with Parkinson's disease and Huntington's chorea; pain; anxiety; AIDS dementia; and Alzheimer's disease. Since the mGluRs can influence levels of alertness, attention and cognition; protect nerve cells from excitotoxic damage resulting from ischemia, hypoglycemia and anoxia; modulate the level of neuronal excitation; influence central mechanisms involved in controlling movement; reduce sensitivity to pain; and reduce levels of anxiety, these compounds can also be used to influence these situations and also find use in learning and memory deficiencies such as senile dementia. mGluRs may also be involved in addictive behavior, alcoholism, drug addiction, sensitization and drug withdrawal (*Science*, 280:2045, 1998), so compounds acting at mGluRs might also be used to treat these disorders.

The current pharmaceutical options for treating neurological disorders tend to be very general and non-specific in their actions in that, although they may reduce the clinical symptoms associated with a specific neurological disorder, they may also negatively impact normal function of the central nervous system of patients. Thus new cellular targets and drugs that are more specific in their actions require to be identified and developed and thus a need remains for chemical compounds that demonstrate specific binding characteristics towards mGluRs.

SUMMARY OF THE INVENTION

It is an object of this invention to provide novel compounds that demonstrate activity at the various metabotropic glutamate receptors (mGluRs). In particular, a compound of Formula I and stereoisomers thereof:

(I)

wherein:

R1 can be an acidic group selected from the group consisting of carboxyl, phosphono, phosphino, sulfono, sulfino, borono, tetrazol, isoxazol, —$CH_2$-carboxyl, —$CH_2$-phosphono, —$CH_2$-phosphino, —$CH_2$-sulfono, —$CH_2$-sulfino, —$CH_2$borono, —$CH_2$-tetrazol, —$CH_2$-isoxazol and higher homologues thereof;

R2 can be a basic group selected from the group consisting of 1° amino, 2° amino, 3° amino, quaternary ammonium salts, aliphatic 1° amino, aliphatic 2° amino, aliphatic 3° amino, aliphatic quaternary ammonium salts, aromatic 1° amino, aromatic 2° amino, aromatic 3° amino, aromatic quaternary ammonium salts, imidazol, guanidino, boronoamino, allyl urea, thiourea;

R3 can be H, aliphatic, aromatic or heterocyclic;

R4 can be an acidic group selected from the group consisting of carboxyl, phosphono, phosphino, sulfono, sulfino, borono, tetrazol, isoxazol;

and pharmaceutically acceptable salts thereof.

DETAILED DESCRIPTION OF THE INVENTION

The terms and abbreviations used in the instant examples have their normal meanings unless otherwise designated. For example "°C." refers to degrees Celsius; "N" refers to normal or normality; "mmol" refers to millimole or millimoles; "g" refers to gram or grams; "mL" means milliliter or milliliters; "M" refers to molar or molarity; "MS" refers to mass spectrometry; "IR" refers to infrared spectroscopy; and "NMR" refers to nuclear magnetic resonance spectroscopy.

As would be understood by the skilled artisan throughout the synthesis of the compounds of Formula I, it may be necessary to employ an amino-protecting group or a carboxy-protecting group in order to reversibly preserve a reactively susceptible amino or carboxy functionality while reacting other functional groups on the compound.

Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4cyanobenzyloxycarbonyl, t-butoxycarbonyl, 2-(4-xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfono)-ethoxycarbonyl, 2-(methylsulfono)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy) benzyloxycarbonyl, isobornyloxycarbonyl, 1-piperidyloxycarbonlyl and the like; benzoylmethylsulfono group, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc), allyloxycarbonyl and benzyloxycarbonyl (CbZ). Further examples of these groups are found in E. Haslam in *Protective Groups in Organic Synthesis,* McOmie, J. G. W., Ed. 1973, at Chapter 2; and Greene, T. W. and Wuts, P. G. M., *Protective Groups in Organic Synthesis,* Second edition; Wiley-Interscience: 1991; Chapter 7.

Examples of such carboxyl-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2'4,4'-tetramethoxybenzhydryl, t-butyl, t-amyl, trityl, 4-methoxytrityl, 4,4'-dimethoxytrityl, 4,4'4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonoethyl, 4-nitrobenzylsulfonoethyl, allyl, cinnamyl, 1-(trimethylsilylmethyl)prop-1-en-3-yl and like moieties. Preferred carboxyl-protecting groups are allyl, benzyl and t-butyl. Further examples of these groups are found in E. Haslam, supra, at Chapter 5; and T. W. Greene and P. G. M. Wuts, supra, at Chapter 5.

The present invention provides a compound of the formula:

(I)

wherein:
R1 can be an acidic group selected from the group consisting of carboxyl, phosphono, phosphino, sulfono, sulfino, borono, tetrazol, isoxazol, —CH$_2$-carboxyl, —CH$_2$-phosphono, —CH$_2$-phosphino, —CH$_2$-sulfono, —CH$_2$-sulfino, —CH$_2$-borono, —CH$_2$-tetrazol, —CH$_2$-isoxazol and higher analogues thereof;

R2 can be a basic group selected from the group consisting of 1° amino, 2° amino, 3° amino, quaternary ammonium salts, aliphatic 1° amino, aliphatic 2° amino, aliphatic 3° amino, aliphatic quaternary ammonium salts, aromatic 1° amino, aromatic 2° amino, aromatic 3° amino, aromatic quaternary ammonium salts, imidazol, guanidino, boronoamino, allyl, urea, thiourea;

R3 can be H, aliphatic, aromatic or heterocyclic;

R4 can be an acidic group selected from the group consisting of carboxyl, phosphono, phlosphino, sulfono, sulfino, borono, tetrazol, isoxazol;

and pharmaceutically acceptable salts thereof.

In particular compounds wherein the compound of Formula I is selected from the group consisting of:

(I)

wherein:
R1 is COOH
R2 is NH$_2$
R3 can be H or methyl or xanthyl or CH$_2$-xanthyl- or —CH$_2$-thioxanthyl- and
R4 is COOH While all of the compounds of Formula I are believed to demonstrate activity at the metabotropic glutamate receptors (mGluRs), certain groups of Formula I compounds are more preferred for such use.

As noted above, this invention includes the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobroric acid, hydriodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quaternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. This invention further encompasses the pharmaceutically acceptable solvates of the compounds of Formula I. Many of the Formula I compounds can combine with solvents such as water, methanol, ethanol and acetonitrile to form pharmaceutically acceptable solvates such as the corresponding hydrate, methanolate, ethanolate and acetonitrilate.

The compounds of the present invention have multiple asymmetric (chiral) centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The prefixes "R" and "S" are used herein as commonly used in organic chemistry to denote the absolute configuration of a chiral center, according to the Cahn-Ingold-Prelog system. The stereochemical descriptor R (rectus) refers to that configuration of a chiral center with a clockwise relationship of groups tracing the path from highest to second-lowest priorities when viewed from the side opposite to that of the lowest priority group. The stereochemical descriptor S (sinster) refers to that configuration of a chiral center with a counterclockwise relationship of groups tracing the path from highest to second-lowest priority when viewed from the side opposite to the lowest priority group. The priority of groups is decided using sequence rules as described by Cahn et al., *Angew. Chem.*, 78, 413–447, 1966 and Prelog, V. and Helmchen, G.; *Angew. Chem. Int. Ed. Eng.*, 21, 567–583, 1982).

In addition to the R,S system used to designate the absolute configuration of a chiral center, the older D-L system is also used in this document to denote relative configuration, especially with reference to amino acids and amino acid derivatives. In this system a Fischer projection of the compound is oriented so that carbon-1 of the parent chain is at the top. The prefix "D" is used to represent the relative configuration of the isomer in which the functional (determining) group is on the right side of the carbon atom at the chiral center and "L", that of the isomer in which it is on the left.

As would be expected, the stereochemistry of the Formula I compounds is critical to their potency as agonists or antagonists. The relative stereochemistry is established early during synthesis, which avoids subsequent stereoisomer separation problems later in the process. Further manipulation of the molecules then employs stereospecific procedures so as to maintain the preferred chirality. The preferred methods of this invention are the methods employing those preferred compounds.

Non-toxic metabolically-labile esters and amides of compounds of Formula I are ester or amide derivatives of compounds of Formula I that are hydrolyzed in vivo to afford said compounds of Formula I and a pharmaceutically acceptable alcohol or amine. Examples of metabolically-labile esters include esters formed with (1–6C)alkanols in which the alkanol moiety may be optionally substituted by a (1–8C)alkoxy group, for example methanol, ethanol, propanol and methoxyethanol. Examples of metabolically-labile amides include amides formed with amines such as methylamine.

According to another aspect, the present invention provides a process for the preparation of a compound of Formula I, or a pharmaceutically acceptable metabolically-labile ester or amide thereof, or a pharmaceutically acceptable salt thereof, which comprises:

(a) hydrolyzing a compound of formula (IIa):

(IIa)

wherein:
R'1 is an acidic group selected from the group consisting of carboxyl, phosphono, phosphino, sulfono, sulfino, borono, tetrazol, isoxazol, —CH₂-carboxyl, —CH₂-phosphono, —CH₂-phosphino, —CH₂-sulfono, —CH₂-sulfino, —CH₂-borono, —CH₂-tetrazol, —CH₂-isoxazol and higher analogues thereof, or a protected form thereof, R3 can be H, aliphatic, aromatic or heterocyclic and R5 represents a hydrogen atom or an acyl group. Preferred values for R5 are hydrogen and (2–6C)alkanoyl groups, such as acetyl; or

(b) deprotecting and hydrolyzing a compound of formula (IIb)

(IIb)

wherein:
R'1 and R3 are as defined above; or (c) hydrolyzing a compound of formula:

(III)

wherein:
R'1 and R3 has the meaning defined above, R6 and R7 each independently represent a hydrogen atom, a (2–6C)alkanoyl group, a (1–4C)alkyl group, a (3–4C)alkenyl group or a phenyl (1–4C)alkyl group in which the phenyl is unsubstituted or substituted by halogen, (1–4C)alkyl or (1–4C)alkoxy, or a salt thereof; or (d) deprotecting a compound of formula:

(IV)

wherein:
R'1 and R3 has the meaning defined above, R8 represents a hydrogen atom or a carboxyl protecting group, or a salt thereof, and R9 represents a hydrogen atom or a nitrogen protecting group;
whereafter, if necessary and/or desired:
  (i) resolving the compound of Formula I;
  (ii) converting the compound of Formula I into a non-toxic metabolically-labile ester or amide thereof; and/or;
  (iii) converting the compound of Formula I or a non-toxic metabolically-labile ester or amide thereof into a pharmaceutically acceptable salt thereof.

The protection of carboxylic acid and amine groups is generally described in McOmie, Protecting Groups in Organic Chemistry, Plenum Press, NY, 1973, and Greene and Wuts, Protecting Groups in Organic Synthesis, 2nd, Ed., John Wiley & Sons, NY. 1991. Examples of carboxyl protecting groups include alkyl groups such as methyl, ethyl, t-butyl and t-amyl; aralkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl, silyl groups such as trimethylsilyl and t-butyldimethylsilyl; and allyl groups such as allyl and 1-trimethylsilylmethyl)prop-1-en-3-yl.

Examples of amine-protecting groups include acyl groups, such as groups of formula R9 CO in which R9 represents (1–6C)alkyl, (3–10C)cycloalkyl, phenyl(1–6C) alkyl, phenyl(1–6C)alkoxy, or a (3–10C)cycloalkoxy, wherein a phenyl group may optionally be substituted by one or two substituents independently selected from amino, hydroxy, nitro, halogeno, (1–6C)alkyl, (1–6C)alkoxy, carboxyl, (1–6C)alkoxycarbonyl, carbamoyl, (1–6C) alkanoylamino, (1–6C)alkylsulphonylamino, phenylsulphonylamino, toluenesulphonylamino, and (1–6C) fluoroalkyl.

The compounds of Formula II are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water and at a temperature in the range of 50 to 200° C.

The compounds of Formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from 50 to 150° C.

The compounds of Formula IV may be deprotected by a conventional method. Thus, an alkyl carboxyl protecting group may be removed by hydrolysis. The hydrolysis may conveniently be performed by heating the compound of Formula IV in the presence of either a base, for example an alkali metal hydroxide such as lithium, sodium or potassium hydroxide, or an alkaline metal hydroxide, such as barium hydroxide, or an acid such as hydrochloric acid. The hydrolysis is conveniently performed at a temperature in the range from 10 to 300° C. An aralkyl carboxyl protecting group may conveniently be removed by hydrogenolysis. The hydrogenolysis may conveniently be effected by reacting the compound of Formula IV with hydrogen in the presence of a Group VIII metal catalyst, for example a palladium catalyst such as palladium on charcoal. Suitable solvents for the reaction include alcohols such as ethanol. The reaction is conveniently performed at a temperature in the range from 0 to 100° C. An acyl, amine protecting group is also conveniently removed by hydrolysis, for example as described for the removal of an alkyl carboxyl protecting group.

The compounds of Formula II may be prepared by reacting a compound of formula:

(V)

with an alkali metal cyanide, such as lithium, sodium or potassium cyanide, and an ammonium halide, such as ammonium chloride, conveniently in the presence of ultrasound. Thus, the ammonium halide is mixed with chromatography grade alumina in the presence of a suitable diluent such as acetonitrile. The mixture is then irradiated with ultrasound, whereafter the compound of Formula V is added, and the mixture is again irradiated. The alkali metal cyanide is then added, followed by further irradiation with ultrasound.

Individual isomers of compounds of Formula II may be made by reacting a compound of the Formula V with the stereoisomers of the chiral agent (S)- and (R)-phenylglycinol and a reactive cyanide such as trimethylsilyl cyanide.

The compounds of Formula III may be prepared by reacting a compound of Formula V with an alkali metal cyanide, such as lithium, sodium or potassium cyanide, and ammonium carbonate or ammonium carbamate. Convenient solvents include water, dilute ammonium hydroxide, alcohols such as methanol, aqueous methanol and aqueous ethanol. Conveniently the reaction is performed at a temperature in the range of from 10 to 150° C. If desired, the compounds of Formula III may then be alkylated, for example using an appropriate compound of formula R6 Cl and/or R7 Cl.

The compounds of Formula V can be prepared by reacting a compound of formula:

(VI)

with a chlorinating agent such as thionyl chloride or phosphorous (V) chloride, followed by reaction with organo copper or organo metal or Grignard reagent derived from R3X or by reaction with ethyl hydrogen malonate in the presence of organolithium, wherein R3 has the meaning defined above and X is halogen.

The compounds of Formula V can also be prepared by oxidizing a compound of formula:

(VII)

under Swern conditions.

The compounds of Formula VI can be prepared from compounds of formula:

(VIII)

by reduction.

When R'1 is $CO_2Me$, this compound can be bought commerically. When R'1 is another substituent, the compound of Formula VIII can be made using standard procedures.

Many of the intermediates described herein, for example the compounds of Formula II, III and IV are believed to be novel, and are provided as further aspects of the invention.

The Formula I compounds of the present invention are agonists or antagonists at certain metabotropic excitatory amino acid receptors (mGluRs). Therefore, another aspect of the present invention is a method of affecting mGluRs in mammals, which comprises administering to a mammal requiring modulated excitatory amino acid neurotransmission a pharmacologically-effective amount of a compound of Formula I. The term "pharmacologically-effective amount" is used to represent an amount of the compound of the invention that is capable of affecting the mGluRs. By affecting, a compound of the invention is acting as an agonist or antagonist. When a compound of the invention acts as an agonist, the interaction of the compound with the excitatory amino acid receptor mimics the response of the interaction of this receptor with its natural ligand (i.e. L-Glutamic acid). When a compound of the invention acts as an antagonist, the interaction of the compound with the excitatory amino acid receptor blocks the response of the interaction of this receptor with its natural ligand (i.e. L-Glutamic acid).

The particular dose of compound administered according to this invention will, of course, be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.001 mg/kg to about 100 mg/kg of the active compound of this invention. Preferably, daily doses will be about 0.05 mg/kg to about 50 mg/kg, more preferably from about 0.1 mg/kg to about 20 mg/kg.

A variety of physiological functions have been shown to be subject to influence by excessive or inappropriate stimulation of excitatory amino acid transmission. The Formula I compounds of the present invention are believed (through their interactions at the mGluRs) to have the ability to treat a variety of neurological disorders in mammals associated with this condition, including acute neurological disorders such as cerebral deficits subsequent to cardiac bypass surgery and grafting, cerebral ischemia (e.g. stroke and cardiac arrest), spinal cord trauma, head trauma, perinatal hypoxia, and hypoglycemic neuronal damage. The Formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's disease. The present invention also provides methods for treating these disorders which comprises administering to a patient in need thereof an effective amount of a compound of Formula I.

The Formula I compounds of the present invention (through their interactions at the mGluRs) are also believed to have the ability to treat a variety of other neurological disorders in mammals that are associated with glutamate dysfunction, including muscular spasms, convulsions, migraine headaches, urinary incontinence, psychosis, drug tolerance, withdrawal, and cessation (i.e. opiates, benzodiazepines, nicotine, cocaine, or ethanol), smoking cessation, anxiety and related disorders (e.g. panic attack), emesis, brain edema, chronic pain, sleep disorders, Tourette's syndrome, attention deficit disorder, and tardive dyskinesia. Therefore, the present invention also provides methods for treating these disorders which comprise administering to a patient in need thereof an effective amount of the compound of Formula I.

The Formula I compounds of the present invention (through their interactions at the mGluRs) are also believed to have the ability to treat a variety of psychiatric disorders, such as schizophrenia, anxiety and related disorders (e.g. panic attack), depression, bipolar disorders, psychosis, and obsessive compulsive disorders. The present invention also provides methods for treating these disorders which comprises administering to a patient in need thereof an effective amount of a compound of Formula I.

The pharmacological properties of the compounds of the invention can be illustrated by determining their effects in various functional in vitro assays. The compounds of the invention were studied in an in vitro assay that measured the inhibition of PI hydrolysis or the formation of cyclic AMP in Chinese hamster ovary cell lines expressing $mGluR_{1\alpha}$, $mGluR_2$ and $mGluR_{4a}$ cloned metabotropic glutamate receptors.

Principle

So far eight different clones of the G-protein-coupled mGluRs have been identified (Knopfel et al., 1995, *J. Med. Chem.*, 38, 1417–1426). These receptors function to modulate the presynaptic release of L-Glutamate, and the postsynaptic sensitivity of the neuronal cell to L-Glutamate excitation. Based on pharmacology, sequence homology and the signal transduction pathway that they activate, the mGluRs have been subclassified into three groups. The $mGluR_1$ and $mGluR_5$ receptors form group I. They are coupled to hydrolysis of phosphatidylinositol (PI) and are selectively activated by (RS)-3,5-dihydroxyphenylglycine (Brabet et al., *Neuropharmacology*, 34, 895–903, 1995). Group II comprises $mGluR_2$ and $mGluR_3$ receptors. They are negatively coupled to adenylate cyclase and are selectively activated by (2S,1'R,2'R,3'R)-2-(2,3-dicarboxycyclopropyl) glycine (DCG-IV; Hayashi et al., Nature, 366, 687–690, 1993). Finally, the mGluR$_1$, mGluR$_6$, mGluR$_7$ and mGluR$_8$ receptors belong to group III. They are also negatively coupled to adenylate cyclase and are selectively activated by (S)-2-amino-4-phosphonylbutyric acid (L-AP4; Knopfel et al., 1995, J. Med. Chem., 38, 1417–1426).

Cell Culture

The Chinese hamster ovary cell lines expressing mGluR$_{1\alpha}$, mGluR$_2$ and mGluR$_{4a}$ receptors have been described previously (Aramori and Nakanishi, Neuron 8, 757–765, 1992; Tanabe et al., Neuron 8, 169–179, 1992; Tanabe et al., J. Neurosci. 13, 1372–1378). They were maintained at 37° C. in a humified 5% $CO_2$ incubator in Dulbecco's Modified Eagle Medium (DMEM) containing a reduced concentration of (S)-glutamine (2 mM) and were supplemented with 1% proline, penicillin (100 U/ml), streptomycin (100 mg/ml) and 10% dialyzed fetal calf serum (all GIBCO, Paisley). Two days before assay $1.8 \times 10^6$ cells were divided into the wells of 24 well plates.

Second Messenger Assays

PI hydrolysis was measured as described previously (Hayashi et al., Br. J. Pharmacol. 107, 539–543, 1992; Hayashi et al., J. Neurosci. 14, 3370–3377, 1994). Briefly, the cells were labeled with [$^3$H]inositol (2 $\mu$Ci/ml) 24 h prior to the assay. For agonist assays, the cells were incubated with ligand dissolved in phosphate-buffered saline (PBS)-LiCl for 20 min, and agonist activity was determined by measurement of the level of $^3$H-labeled mono-, bis- and tris-inositol phosphates by ion-exchange chromatography. For antagonist assays, the cells were preincubated with the ligand dissolved in PBS-LiCl for 20 min prior to incubation with ligand and 10 $\mu$M (L)-Glutamic acid for 20 min. The antagonist activity was then determined as the inhibitory effect of the (L)Glutanmic acid-mediated response. The assay of cyclic AMP formation was performed as described previously (Hayashi et al., Br. J. Pharmacol. 107, 539–543, 1992; Hayashi et al., J. Neurosci. 14, 3370–3377, 1994). Briefly, the cells were incubated for 10 min in PBS containing the ligand and 10 $\mu$M forskolin and 1 mM 3-Isobutyl-1-methyxanthine (IBMX; both Sigma, St. Louis, Mo., USA). The agonist activity was then determined as the inhibitory effect of the forskolin-induced cyclic AMP formation. For antagonist assay, the cells were preincubated with ligand dissolved in PBS containing 1 mM IBMX for 20 min prior to a 10 min incubation in PBS containing the ligand, 20 $\mu$M (mGluR$_2$) or 50 $\mu$M (mGluR$_{4a}$), (L)-Glutamic acid, 10 $\mu$M Forskolin and 1 $\mu$M IBMX.

Results

Figure 1:
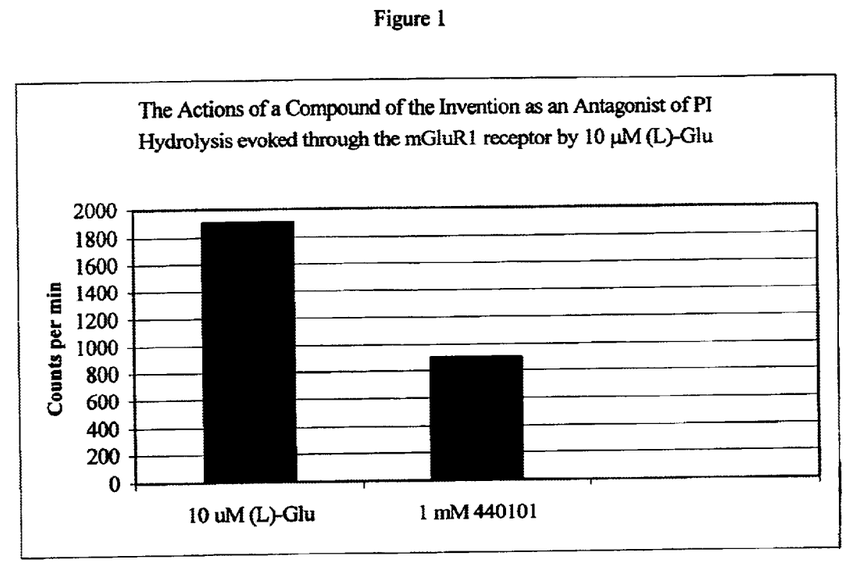
FIG. 1: The actions of a compound of the invention as an antagonist of PI hydrolysis evoked through the mGluR1 receptor by 10 $\mu$M (L)-Glu.

Some of the compounds of the invention were tested for antagonist activity against Chinese hamster ovary cell lines expressing mGluR$_{1\alpha}$, mGluR$_2$ and mGluR$_{4a}$ cloned mGluRs at a concentration of 1 mM. When tested as antagonists of the increase in PI hydrolysis evoked by 10 $\mu$M (L)-Glutamic acid, some compounds of the invention effectively blocked this increase in PI hydrolysis by an action at the mGluR$_{1\alpha}$receptor. The data for one of the compounds of the invention is shown in FIG. 1 below.

According to another aspect, the present invention provides a method of modulating one or more metabotropic glutamate receptor functions in a warm-blooded mammal which comprises administering an effective amount of a compound of Formula I, or a non-toxic metabolically-labile ester or amide thereof, or a pharmaceutically acceptable salt thereof.

The compounds of the present invention are preferably formulated prior to administration. Therefore, another aspect of the present invention is a pharmaceutical formulation comprising a compound of Formula I and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material that acts as a vehicle, excipient, or medium for the active ingredient.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. The present invention also provides pharmaceutical compositions containing compounds as disclosed in the claims in combination with one or more pharmaceutically acceptable, inert or physiologically active, diluent or adjuvant. The compounds of the invention can be freeze-dried and, if desired, combined with other pharmaceutically acceptable excipients to prepare formulations for administration. These compositions may be presented in any form appropriate for the administration route envisaged. The parenteral and the intravenous route are the preferential routes for administration.

Compounds of the general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents one or more flavouring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compound(s) of the general Formula I may be administered, together or separately, in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compound(s) of general Formula I may be administered, together or separately, parenterally in sterile medium. The drug, depending on the vehicle and concentration used, can either be suspended or dissolved in the vehicle. Advantageously, adjuvants such as local anaesthetics, preservatives and buffering agents can be dissolved in the vehicle.

The dosage to be administered is not subject to defined limits, but it will usually be an effective amount. It will usually be the equivalent, on a molar basis of the pharmacologically active free form produced from a dosage formulation upon the metabolic release of the active free drug to achieve its desired pharmacological and physiological effects. The compositions are preferably formulated in a unit dosage form each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 |

The above ingredients are mixed and filled into hard gelatin capsules in 460 mg quantities.

Formulation 2
A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 |

The components are blended and compressed to form tablets each weighing 665 mg.

Formulation 3
An aerosol solution is prepared containing the following components:

| | Weight % |
|---|---|
| Active Ingredient | 0.25 |
| Ethanol | 29.75 |
| Propellant 22 (Chlorodifluoromethane) | 70.00 |
| Total | 100 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| | Quantity (mg/tablet) |
|---|---|
| Active Ingredient | 60 |
| Starch | 45 |
| Microcrystalline cellulose | 35 |
| Polyvinylpyrrolidone | 4 |
| Sodium carboxymethyl starch | 4.5 |
| Magnesium stearate | 0.5 |
| Talc | 1.0 |
| Total | 150 |

The active ingredient, starch and cellulose are passed through a No. 45 mesh U.S. sieve and mixed thoroughly. The solution of polyvinylpyrrolidone is mixed with the resultant powders that are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| | Quantity (mg/capsule) |
|---|---|
| Active Ingredient | 80 |
| Starch | 59 |
| Microcrystalline cellulose | 59 |
| Magnesium stearate | 2 |
| Total | 200 |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| | Quantity (mg/suppository) |
|---|---|
| Active Ingredient | 225 |
| Saturated fatty acid glycerides | 2000 |
| Total | 2225 |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 mL dose are made as follows:

| | |
|---|---|
| Active Ingredient | 50 mg |
| Sodium carboxymethyl cellulose | 50 mg |
| Syrup | 1.25 mL |
| Benzoic acid solution | 0.10 mL |
| Flavour | q.v. |
| Color | q.v. |
| Purified water to total | 5 mL |

The medicament is passed through a No. 45 mesh U.S. sieve and mixed with the sodium carboxymethyl cellulose and syrup to form a smooth paste. The benzoic acid solution flavor and color are diluted with some of the water and added, with stirring. Sufficient water is then added to produce the required volume.

Formulation 8
An intravenous formulation may be prepared as follows:

|  | Quantity |
|---|---|
| Active Ingredient | 100 mg |
| Mannitol | 100 mg |
| 5 N Sodium hydroxide | 200 mL |
| Purified water to total | 5 mL |

Formulation 9
A topical formulation may be prepared as follows:

|  | Quantity |
|---|---|
| Active Ingredient | 1–10 g |
| Emulsifying Wax | 30 g |
| Liquid Paraffin | 20 g |
| White soft paraffin to | 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation 10
Sublingual or buccal tablets, each containing 10 mg of active ingredient, may be prepared as follows:

|  | Quantity (mg/tablet) |
|---|---|
| Active Ingredient | 10.0 |
| Glycerol | 210.5 |
| Water | 143.0 |
| Sodium Citrate | 4.5 |
| Polyvinyl Alcohol | 26.5 |
| Polyvinylpyrrolidone | 15.5 |
| Total | 410.0 |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, for example, U.S. Pat. No. 5,023,252, issued Jun. 11, 1991) herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions that can transiently open the blood-brain barrier.

EXAMPLES

The following Examples illustrate the invention. The following abbreviations are used in the Examples: EtOAc, ethyl acetate; THF, tetrahydrofuran; EtOH, ethanol; TLC, thin layer chromatography; GC, gas chromatography; HPLC, high pressure liquid chromatography; m-CPBA, m-chloroperbenzoic acid; Et$_2$O, diethyl ether; DMSO, dimethyl sulfoxide; DBU, 1,8-diazabicyclo-[5.4.0]undec-7-ene, MTBE, methyl t-butyl ether; FDMS, field desorption mass spectrometry and r.t., room temperature.

Example 1
Synthesis of Cubanylglycinates IGT, 1.0 series

Preparation 1: 4-methoxycarbonylcubane carboxylic acid

A solution of cubane dimethyl ester (6.0 g, 27.24 mmol) in 182 mL of dry THF is stirred under $N_2$ at room temperature. A solution of methanolic NaOH (26.7 mmol, 10.7 mL 2.5 M) is added dropwise from a pressure equalized addition funnel and the resulting solution stirred at room temperature for 16 h. The mixture is evaporated under reduced pressure at r.t., the residue is taken up in 66 mL of water and extracted with 3×25 mL of chloroform. The aqueous layer is acidified to pH 3 with concentrated HCl and extracted with 3×30 mL of chloroform. The combined organic layers were dried over magnesium sulphate, filtered and evaporated to give (2) 182–183° C.: $^1$H NMR (CDCl$_3$) δ 3.72 (s, 3H), 4.27 (m, 6H). Yield 5.1 g (91%).

Preparation 2: 4-methoxycarbonyl-1-(hydroxymethyl)cubane

The mono acid (2) (0.48 g) is dissolved in dry THF (5 mL) and cooled to −70° C. A solution of BH$_3$ in THF is added slowly with stirring. The reaction mixture is stirred at −78° C. for 4 hrs and allowed to come to room temperature. Water (3 mL) is added and stirred for 30 min, potassium carbonate (0.85 g) is added and the solution extracted with Et$_2$O. The organic phase is dried over magnesium sulfate and evaporated to give the alcohol (3) 0.46 g (100%) m.p. 83–85° C. $^1$H NMR(200 MHz, solvent) δ: 1.58 (s, 1H), 3.62 (s, 3H), 3.72 (s, 2H), 3.81 (m, 3H), 4.1 (m, 3H).

Preparation 3: 4-methoxycarbonyl-1-(formyl)cubane

DMSO (0.7 mL, 9.68 mmol) is added to oxalyl chloride (0.42 mL, 4.84 mmol) in 12 mL of CH$_2$Cl$_2$ at −78° C. The alcohol (3) (0.46 g, 2.42 mmol) in 3 mL CH$_2$Cl$_2$ is added and stirred at −78° C. for 1.5 h. Triethylamine,(2.0 mL, 14.4 mmol) is added and the mixture is allowed to come to 0° C. Saturated ammonium chloride solution is added and the phases separated, the aqueous layer is extracted with CH$_2$Cl$_2$ and the combined organic layers are dried (MgSO$_4$), then evaporated to give crude product which is purified by flash chromatography (1:1 hexanes:diethyl ether) to give 0.35 g (76%) of pure product (4). $^1$H NMR (200 MHz, solvent) δ: 3.7 (s, 3H), 4.2 (m, 3H), 4.32 (m, 3H), 9.72 (s, 1H).

Preparation 4: 4-methoxycarbonyl-1-[2'-hydroxy-1'-phenylethyl]methylnitrilecubane (R)-phenylglycinol (257 mg, 1.87 mmol) is added to a solution of the aldehyde (4) (0.35 g, 1.84 mmol) in 14 mL of methanol. The solution is cooled to 0° C. and TMSCN (0.49 mL, 3.68 mmol) is added and the mixture stirred at 0° C. overnight. Evaporation of the solvent leaves a residue which is purified by chromatography (diethyl ether:hexanes, 3:1) to give 0.48 g (77%) of pure product (5). $^1$H NMR (CDCl$_3$) δ: 2.23 (s, 1H), 2.6 (br, 1H), 3.5–3.75 (m, 2H), 3.7 (s, 3H), 3.9 (m, 3H), 4.11 (dd, 1H), 4.2 (m, 3H), 7.3 (s, 5H).

Preparation 5: 4-carboxy-1-cubanylglycine

Lead acetate (0.69 g, 1.57 mmol) is added to a stirred solution of nitrile (5) (0.48 g, 1.42 mmol) in dry methanol/dichloromethane 1:1 (12 mL). After 10 min 10 mL of water is added and the suspension filtered through celite. The organic layer is dried and evaporated to give the crude imine. The crude imine is refluxed with 6N HCl (30 mL) for 6 hr. The solution is evaporated to dryness and placed on anion exchange resin, elutina with 1N acetic acid to yield the product (6). mp. 241° C. (dec.) $^1$H NMR (D$_2$O) δ 3.96 (s, 1H), 4.01 (m, 3H), 4.14 (m, 3H).

Example 2

Preparation 1: 4-methoxycarbonylcubane carboxylic acid

A solution of cubane dimethyl ester (6.0 g, 27.24 mmol) in 182 mL of dry THF is stirred under $N_2$ at r.t. a solution of methanolic NaOH (26.7 mmol, 10.7 mL 2.5 M) is added dropwise from a pressure equalized addition funnel and the resulting solution stirred at r.t. for 16 h. The mixture is evaporated under reduced pressure at r.t., the residue is taken up in 66 mL of water and extracted with 3×25 mL of chloroform. The aqueous layer is acidified to pH 3 with concentrated HCl and extracted with 3×30 mL of chloroform. The combined organic layers were dried over magnesium sulphate, filtered and evaporated to give (2) 182–183° C.: $^1$H NMR (CDCl$_3$) δ 3.72 (s, 3H), 4.27 (m, 6H). Yield 5.1 g (91%).

Preparation 2: 4-methoxycarbonylcubane-1-carbonyl chloride

The monomethyl ester (2) (1.37 g, 6.65 mmol) is dissolved in 15 mL of thionyl chloride and gently refluxed overnight. The thionyl chloride is evaporated off and the resultant residue containing (3) was used immediately without further purification.

Preparation 3: 4-methoxycarbonylcubane-1-methyl ketone

A suspension of copper iodide (1.49 g, 7.83 mmol) in 30 mL of dry THF is stirred at 0° C. Methyl lithium (15.75 mmol, 11.2 mL of 1.4 M) was added and stirred at 0° C. for 30 min, then cooled to −78° C. A solution of 1.6 g, 7.12 mmol of (3) in 10 mL dry THF is added and the resultant mixture stirred for 1 h. at −78° C. The mixture was quenched with saturated ammonium chloride solution (15 mL) and extracted with 3×30 mL of diethyl ether. The combined organic layers were dried over magnesium sulphate, filtered and evaporated to give crude (4). The product was purified by silica chromatography (hexanes:ethyl acetate, 2:1) to give 1.0 g of product (yield 69/%). m.p. 87–89° C. $^1$H NMR (CDCl$_3$) δ 2.17 (s, 3H), 3.7 (s, 3H), 4.21 (m, 6H).

Preparation 4: 4methoxycarbonylcubane-1-methyl-1-(5,5'-hydantoin)

A solution of the methyl ketone (4) (1.0 g, 4.9 mmol) in 40 mL of ethanol and 5.8 mL of 1 N NaOH, is stirred at 70° C. for 4 h. The resulting solution is evaporated to dryness under reduced pressure and redissolved in 1:1 ethanol:water (20 mL). To this solution is added potassium cyanide (0.35 g, 5.4 mmol) and ammonium carbonate (0.96 g, 9.8 mmol) and the mixture heated in a sealed tube at 85° C. for 24 h. The reaction is cooled, acidified with 6 N HCl and reduced in volume until a precipitate forms. The precipitate is filtered and the filtrate evaporated to dryness and extracted with ethyl acetate. The solvent is evaporated and the product combined with the residue from above to give (5) as a white solid. Yield 0.95 g (75%) m.p. 244–248° C. NMR $^1$H (DMSO) δ 1.18 (s, 3H) 3.9 (m, 3H), 4.0 (m, 3H), 8.1 (s, 1H), 10.6 (s, 1H).

Preparation 5: 4-carboxycubane-1-methylglycine

The hydantoin (5) (0.95 g, 3.65 mmol) is dissolved in 30 mL of 2 N NaOH and heated at 170° C. in a sealed tube for 20 h. The reaction is cooled and filtered to remove precipitate and the filter cake washed with 3×10 mL of water. The combined aqueous washings are evaporated to give crude (6) which is applied to Spectrum 1×4 anion exchange resin, eluted with 0.5 N acetic acid. Isolation by evaporation and crystallization gives (6) as colorless crystals. m.p. >250° C. (decomp.), NMR $^1$H (D$_2$O) δ 1.38 (s, 3H), 3.95 (s, 6H).

Example 3

Preparation 1: 4-methoxycarbonylcubane-1-acetyl ethylcarboxylate n-butyl lithium (34.83 mmol, 23.5 mL of 1.5 M) is added dropwise to a stirred solution of ethyl hydrogen malonate (2.32 g, 17.41 mmol) in 80 mL of dry THF under N$_2$ at −78° C. The mixture was warmed to −30° C. over 0.5 h and then re-cooled to −78° C. The acid chloride of cubane monomethyl ester from example (2) above (2.35 g, 10.46 mmol) in 7 mL of THF is added dropwise to the stirred solution. The reaction is warmed slowly to r.t and stirred for a further 1 h. The solution is poured into 50 mL of 1 N HCl and extracted with 3×50 mL of diethyl ether. The combined organic extracts are further extracted with 20 mL of saturated sodium hydrogen carbonate and brine, dried over magnesium sulphate, filtered and evaporated to give crude (2). The product is purified by column chromatography on silica with hexanes:ethyl acetate 2:1 to yield 2.5 g (86%) of (2). $^1$H NMR (CDCl$_3$) δ 1.2 (t, 3H) 3.4 (s, 2H), 3.65 (s, 3H), 4.2 (m, 8H).

Preparation 2: 4-methoxycarbonylcubane-1-(thioxanthyl)-acetyl ethylcarboxylate cubane-β-ketoester (2) (1.15 g, 4.16 mmol) and thioxanthene-9-ol (0.88 g, 4.1 mmol) are dissolved in 18 mL of a 1:1 mixture of ethanol:acetic acid and stirred at r.t. for 3 days. The resulting crystalline solid was filtered off to yield 1.52 g (77%) of pure (3) m.p. 147–149° C. $^1$H NMR (CDCl$_3$) 1.00 (t, 3H), 3.24 (s, 3H), 3.75 (m, 3H), 3.9 (q, 2H), 4.0 (m, 3H), 4.6 (d, 1H), 5.0 (d, 1H), 7.3 (m, 8H).

Preparation 3: 4-carboxycubane-1-methylthioxanthylketone

The thioxanthylcubane adduct (3) (1.69 g, 3.57 mmol) is dissolved in ethanol 33 mL and 8.7 mL of 1 N NaOH and heated at 70° C. for 4 h. The resulting solution is evaporated and redissolved in 25 mL of water, acidified with 6 N HCl and extracted with 3×50 mL of diethyl ether. The combined organic layers are dried over magnesium sulphate, filtered and concentrated to give a crude product containing (4). Chromatography on silica using ethyl acetate gives 1.26 g (88%) of (4) $^1$H NMR (CDCl$_3$) δ 2.8 (d, 2H), 3.8 (m, 3H), 4.0 (m, 3H), 4.7 (t, 1H), 7.3 (m, 8H), 9.5 (br, 1H).

Preparation 4: 4-carboxycubane-1-thioxanthyl-1-(5,5'-hydantoin)

The thioxanthyl cubane ketone (4) (1.24 g, 3.22 mmol) is dissolved in 1:1 ethanol:water (20 mL). Potassium cyanide (0.522 g, 8.0 mmol) and ammonium carbonate (1.39 g, 14.4 mmol) are added and the solution heated in a sealed tube at 85° C. for 65 h. The reaction is cooled and acidified with 2 N HCl and extracted with 3×40 mL of ethyl acetate. The organic layers are combined, dried over magnesium sulphate, filtered and evaporated to give (5) 1.3 g (88%) as a crude product. This material was hydrolyzed in the next step without purification. $^1$H NMR (CD$_3$OD) δ 1.7 (m, 1H), 2.7 (m, 1H), 3.8 (m, 3H), 4.0 (m, 3H), 4.3 (m, 1H), 7.4 (m, 8H).

Preparation 3: 4-carboxycubane-1-thioxanthyl lglycine

The hydantoin adduct (5) (300 mg, 0.65 mmol) is taken up in 1 N NaOH (10 mL) and heated at 170° C. for 20 h in a sealed tube. The mixture is cooled and the pH adjusted with 6 N HCl to between 7 and 8. The precipitate formed is filtered and washed with water. The combined filtrate and washings are combined and evaporated to dryness. The resulting residue is purified by column chromatography and finally by reverse phase chromatography to yield (6) as colorless crystals. 70 mg. $^1$H NMR (CD$_3$OD+D$_2$O) δ 2.3 (m, 2H), 3.9 (s, 6H), 4.4 (m, 1H), 7.4 (m, 8H).

We claim:

1. A compound of the formula:

(I)

wherein:
R1 is carboxyl;
R2 is a basic group selected from the group consisting of 1° amino, 2° amino, and 3° amino;
R3 is CH$_2$-thioxanthyl;
R4 is carboxyl; and pharmaceutically acceptable salts thereof.

2. A compound as claimed in claim 1, wherein R2 is NH$_2$.

3. A process for the preparation of a compound of Formula I as claimed in claim 1, or a pharmaceutically acceptable metabolically-labile ester or amide thereof, or a pharmaceutically acceptable salt thereof, which comprises:

(a) hydrolyzing a compound of formula:

(IIa)

wherein:
R'1 is selected from the group consisting of carboxyl, or a protected form thereof, R3 is CH$_2$-thioxanthyl and R5 represents a hydrogen atom or an acyl group, and wherein preferred values for R5 are hydrogen and (2–6C) alkanoyl groups, such as acetyl; or

(b) deprotecting and hydrolyzing a compound of formula (IIb)

(IIb)

wherein:
R'1 and R3 are as defined above; or

(c) hydrolyzing a compound of formula:

(III)

wherein:
R6 and R7 each independently represents a hydrogen atom, a (2–6C) alkanoyl group, a (1–4C)alkyl group, a (3–4C)alkenyl group or a phenyl (1–4C)alkyl group in which the phenyl is unsubstituted or substituted by halogen, (1–4C)alkyl or (1–4C)alkoxy, or a salt thereof, R'1 and R3 are as defined above; or (d) deprotecting a compound of formula:

(IV)

wherein:
R8 represents a hydrogen atom or a carboxyl protecting group, or a salt thereof, and R9 represents a hydrogen atom or a nitrogen protecting group, R'1 and R3 are as defined above;

whereafter, if necessary and/or desired:
(i) resolving the compound of Formula I;
(ii) converting the compound of Formula I into a non-toxic metabolically-labile ester or amide thereof; and/or
(iii) converting the compound of Formula I or a non-toxic metabolically-labile ester or amide thereof into a pharmaceutically acceptable salt thereof.

4. A pharmaceutical formulation, which comprises a compound as claimed in claim 1 and a pharmaceutically acceptable carrier, diluent or excipient.

5. A method of modulating one or more metabotropic glutamate receptor functions in a warm blooded mammal, comprising administering an effective amount of a compound of formula (I) as claimed in claim 1 to a warm blooded mammal in need thereof.

6. A compound according to claim 1, wherein R1 is —COOH, R2 is —NH2, R3 is —CH$_2$-thioxanthyl and R4 is COOH.

7. A method of treating a neurological disease or disorder in a warm blooded mammal comprising administering an effective amount of the compound of formula (I) according to claim 1 to a warm blooded mammal in need thereof, wherein said neurological disease or disorder is selected from the group consisting of cerebral deficits subsequent to cardiac bypass surgery and grafting, cerebral ischemia, stroke, cardiac arrest, spinal cord trauma, head trauma, perinatal hypoxia, and hypoglycemic neuronal damage, Alzheimer's disease, Huntington's Chorea, amyotrophic lateral sclerosis, AIDS-induced dementia, ocular damage, retinopathy, cognitive disorders, idiopathic and drug-induced Parkinson's disease, muscular spasms, convulsions, migraine headaches, urinary incontinence, psychosis, drug tolerance, withdrawal, and cessation, smoking cessation, anxiety disorders, emesis, brain edema, chronic pain, sleep disorders, Tourette's syndrome, attention deficit disorder, and tardive dyskinesia.

8. A method of treating a psychiatric disease or disorder in a warm blooded mammal comprising administering an effective amount of the compound of formula (I) according to claim 1 to a warm blooded mammal in need thereof, wherein said psychiatric disease or disorder is selected from the group consisting of schizophrenia, anxiety disorders, depression, bipolar disorders, psychosis, and obsessive compulsive disorders.

9. The method according to any one of claim 5, 7 or 8 wherein said compound is

10. A method of treating cerebral ischemia, stroke and cardiac arrest in a warm blooded mammal comprising administering an effective amount of the compound:

to a warm blooded mammal in need thereof.

* * * * *